(12) United States Patent
Vandenabeele et al.

(10) Patent No.: US 6,534,317 B1
(45) Date of Patent: Mar. 18, 2003

(54) USE OF ISOCYANATES FOR ASSAYING NUCLEOPHILIC FUNCTIONS IN THE FORM OF TRACES IN WET MEDIUM

(75) Inventors: Odile Vandenabeele, Montpellier (FR); Laurent Garrelly, Gailhan (FR); Auguste Commeyras, Clapiers (FR); Louis Mion, Montpellier (FR)

(73) Assignee: Picometrics S.A., Ramonville (FR)

( * ) Notice: Subject to any disclaimer, the term of this patent is extended or adjusted under 35 U.S.C. 154(b) by 0 days.

(21) Appl. No.: 09/508,787

(22) PCT Filed: Sep. 16, 1998

(86) PCT No.: PCT/FR98/01984

§ 371 (c)(1),
(2), (4) Date: May 8, 2000

(87) PCT Pub. No.: WO99/14588

PCT Pub. Date: Mar. 25, 1999

(30) Foreign Application Priority Data

Sep. 16, 1997 (FR) .............................................. 97 11508

(51) Int. Cl.$^7$ .............................................. G01N 33/00
(52) U.S. Cl. ...................................... 436/109; 436/161
(58) Field of Search .......................................... 436/161

(56) References Cited

U.S. PATENT DOCUMENTS

| | | | | |
|---|---|---|---|---|
| 2,764,592 A | * | 9/1956 | Seeger et al. ................ | 548/171 |
| 3,506,698 A | * | 4/1970 | Jelinek ........................... | 558/3 |
| 3,884,951 A | * | 5/1975 | Oswald ....................... | 560/357 |
| 3,891,670 A | | 6/1975 | Kanaoka et al. | |
| 4,125,376 A | | 11/1978 | Razulis | |
| 4,335,247 A | * | 6/1982 | Takatori et al. ............. | 548/140 |
| 4,423,076 A | * | 12/1983 | Laki ........................... | 424/322 |
| 4,698,438 A | * | 10/1987 | Blaisdell et al. ................ | 558/3 |
| 4,840,919 A | | 6/1989 | Attar | |
| 4,883,903 A | * | 11/1989 | Roger ........................ | 560/137 |
| 5,284,962 A | * | 2/1994 | Rensi ......................... | 549/438 |
| 5,354,689 A | | 10/1994 | Streicher | |

FOREIGN PATENT DOCUMENTS

| | | | |
|---|---|---|---|
| CH | 662659 A | * | 10/1987 |
| EP | 0 348 826 | | 1/1990 |

OTHER PUBLICATIONS

Lehotav et al., J. Liq. Chromatogr., 1992, 15, p. 307.*
Andersson et al., J. Chromatogr., 1984, 312, p. 482.*
Lindahl et al., J. Chromatogr., 1993, 643, p. 35.*
Sahasrabuddhey et al., Analyst, 1999, 124, 1017–21.*

* cited by examiner

*Primary Examiner*—Jill Warden
*Assistant Examiner*—Yelena Gakh
(74) *Attorney, Agent, or Firm*—Young & Thompson

(57) ABSTRACT

A method for detecting traces of pollutant in aqueous media, wherein the method includes the use of isocyanates to react on the nucleophilic functions in the form of trace amounts in a wet medium. The method for assaying nulceophilic functions in a wet medium includes the following steps: adding isocyanates to an aqueous solution of basic pH containing the nucleophilic functions to be tested; maintaining the solution for an interval ranging from a few minutes to several dozens of minutes at a temperature lower than 100° C.; and assaying the resulting carbamate, thiocarbamate or urea.

5 Claims, 4 Drawing Sheets

USE OF ISOCYANATES FOR ASSAYING NUCLEOPHILIC FUNCTIONS IN THE FORM OF TRACES IN WET MEDIUM

TECHNICAL FIELD

The invention involves a new process for the derivation of thiols, phenols, oxides, and primary and secondary amines in an aqueous solution for the purpose of quantitatively analyzing them under High Performance Liquid Chromatography (otherwise known as HPLC).

The present invention is related to processes for quantitatively analyzing mixtures including a compound bearing a nucleophilic group in a trace amount in an aqueous medium.

A particular application of the invention is the detection of traces of pollutants in aqueous or aqua organic environments.

The detection of pollutants is given in the present description as an example illustrating one of the applications of the invention.

BACKGROUND ART

The detection of numerous compounds present in trace amounts in aqueous or aqua organic environments is desirable in order to detect useful compounds, for which it is desired to determine their concentration or presence, or to detect contaminant compounds, also called, the "micropollutants", which even in extremely low concentrations can have a negative impact on the environment and public health. Among these compounds, the detection and the quantification of carrier compounds of nucleophilic functions is particularly interesting, for example, phenols, oximes, thiols, amines.

The chemical industries among others, using compounds based on sulfur, phenols, oximes or amines, are naturally the important sources of these products. These elements can thus be present in the environment in the uncombined form, or in the precursor chemical compounds.

A significant source is created by pesticides. Certain pesticides in fact contain the nucleophilic functions cited above, in the uncombined or precursory form. When these functions are released by hydrolysis in the environment, they can lead to metabolites that are more toxic than the original pollutants.

The numerous molecules of biological interest (hormones, amino acids, neurotransmitters, etc.) are also carriers of these functions. These compounds are found in products of the agro-food industries and physiological liquids of living organisms.

In each of these cases, the quantitative analysis of these nucleophilic functions is desirable for reasons of medical diagnostics, the quality of the food, or the pollution index.

When their concentration is high (greater than 0.1 g/l), their quantitative analysis can be direct. Numerous methods are thus known in this area and are currently being used.

When their concentration is lower (typically less than a milligram per liter) and when a great precision of the quantitative analysis is necessary, the derivation of the nucleophilic functions that are sought after produces an effective solution to detect lower concentrations. The derivation consists in the creation of a covalent bond between the function studied and another chemical group for the purpose of forming a new entity that can be quantitatively analyzed by a traditional method. The increase of the detectability is linked to physiochemical properties of the deriving compound (increase of the molar extinction coefficient, increase of fluorescence, etc.).

Currently, the quantification and the identification of the chemical types present in trace amounts in a humid or aqueous environment is not easily realized as a rule, as far as the phenols, thiols, oximes are concerned. In this case, global methods can be resorted to which allow for example an estimation of the total concentration of phenols without it being possible to identify the different molecules present.

As far as the amines are concerned, several traditional methods for derivation are known. The chemical functions generally used in order to derive these amines in regard to their quantitative analysis are aldehydes, acid chlorides, acid anhydrides, carbamates (as a chemical function).

These methods have variable limits and disadvantages, such as low stability of the starting materials and derivatives obtained, specific reactivity to certain amines, the need for expensive material exclusively dedicated to these analyses.

In addition, no method exists for the simultaneous derivation applicable to all of the thiols, phenols, oximes, amines. U.S. Pat. No. 5,354,689 by Streicher describes a process that functions by using an excess of amines in order to look for traces of isocyanates, which is the opposite of the process according to the invention. Moreover, the process according to the US patent functions in an organic environment and not in an aqueous environment.

The patent CH 662 659 intends to quantitatively analyze the isocyanates which result from the manufacture of urethanes. The process according to the CH patent functions when dry.

The U.S. Pat. No. 3 891 670 Kanaoka describes a process that does not function with isocyanates. This patent does not involve amine functions.

SUMMARY OF THE INVENTION

The present invention corrects these shortcomings by providing a process for the derivation of compounds in a trace amount including a nucleophilic group in an aqueous medium for the purpose of quantitative analysis by traditional separative methods. The present invention provides a process for obtaining a urea or a carbamate entity by reaction of compounds having a nucleophilic group in an aqueous medium.

According to a second purpose of the invention, a simple device can be designed that uses this process and is economically fabricated.

Finally, according to a third purpose of the invention, the quantitative analysis can be performed on a very large range of compounds present in a humid environment in trace amounts.

The object of the present invention is the use of isocyanates to react to compounds having a nucleophilic group in an aqueous medium in which the nucleophilic groups can be, among others, phenols, thiols, oximes, and amines.

The very strong reactivity of isocyanates to water is known. However, it is totally unexpected to obtain an even stronger reactivity of the isocyanates to the nucleophilic groups. As such, there is a very unique reaction of compounds in a trace amount in a aqueous environment.

In the literature, there is a very strong prejudice against the use of isocyanates in an aqueous or aqua organic environment, due to their very strong reactivity (such as, "Organic Chemistry", $2^{nd}$ Edition, Ray P. Brewster, 1953, pp 559, and in "Reactions of 1,3-Bis(2-chloroethy-1-nitrosourea and 1-(2-chloroethyl)-3-cyclohexyl-1- nitrosourea in Aqueous Solution", Weinkam, Huey Shin Lin, Journal of Medicinal Chemistry, 1979, Vol. 22, No. 10, pp. 1193–1198). In fact, it is recommended to use only the isocyanates in solvents without water, or even traces of water.

In addition, the strong reactivity to water leads to storing them exclusively in an anhydrous environment, and to keep them in a dry place to preserve them.

The present invention obtains a completely unexpected effect which is the predominant reactivity of the isocyanates to the nucleophilic groups, even in the trace amounts, in an aqueous environment. As a result, it is possible to obtain a very simple and economical process for quantitative analysis based on this usage.

Nitrosourea is a masked, stable isocyanate which can act as an isocyanate reservoir because of its decomposition in an aqueous environment. The nitrosourea will decompose into an intermediate isocyanate and this intermediate isocyanate will react to the nucleophilic groups.

Nitrosoureas have the advantage of easily decomposing in molecular engineering, thus they are able to be conducted for the synthesis of very variable isocyanates suited to specific needs, contrary to the uncombined isocyanates whose manufacturing is delicate.

Nitrosourea is a precursor of isocyanates. This usage allows numerous industrial applications, one of which is the quantitative analysis of diverse functions, and also the creation of a quantitative analysis kit containing dry products that are very stable in storage and very inexpensive to manufacture.

The invention presented here also provides a process for the quantitative analysis of nucleophilic functions in an aqueous or aqua organic environment wherein it consists of the phases:
  adding isocyanates to an aqueous solution having a basic pH containing the nucleophilic function to be quantitatively analyzed,
  maintaining the solution over a duration of several minutes to several dozen minutes at a temperature less than 100° C.,
  quantitative analysis of carbamate, thiocarbamate or the urea obtained.

Quantitative analysis is an extensive industrial application of the use of the reactivity of isocyanates to nucleophilic groups in an aqueous environment.

As mentioned above, there is indeed a process for the quantitative analysis of the nucleophilic functions in spite of the fact that contrary to the recommendations for use, the isocyanates are used in an aqueous environment.

The duration of the quantitative analysis will be a function of the type of isocyanate used.

According to a specific claim, the process for quantitative analysis of nucleophilic functions is characterized in that the quantitative analysis of carbamate (R1—NH—CO—XR' with X=O or ON=C), of thiocarbamate (R1—NH—CO—SR') or of the urea obtained (R1—NH—CO—NHR') is done by HPLC (High Performance Liquid Chromatography).

This device allows the use in the process of a detection by a separate traditional method.

The invention also is intended to include a device for quantitative analysis of nucleophilic functions in an aqueous or aqua organic environment, using a process according to the preceding claims.

A device of this type, a "quantitative analysis kit" allows the simple implementation of the process in various uses, with an easy and lasting storage of these reagents.

BRIEF DESCRIPTION OF THE DRAWINGS

The description that follows, made in regard to the drawings and attached examples for the purpose of explaining and not at all restrictive, makes it possible to better understand the advantages, goals and characteristics of the invention.

DETAILED DESCRIPTION OF THE INVENTION

Figure 1:
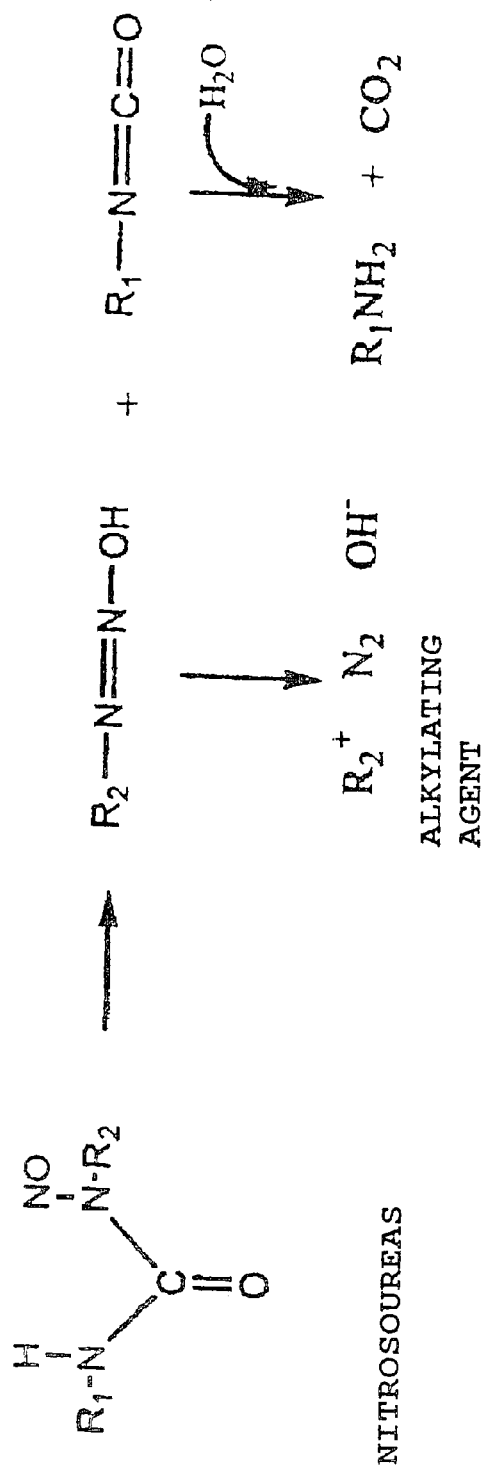
FIG. 1 shows the equation for decomposition of the nitrosourea in water.

According to the equation given in FIG. 1, the mechanism for decomposition of nitrosoureas in water at a basic pH provides an alkylating agent R2+ and an isocyanate R1—N=C=O that hydrolyzes in an aqueous solution in order to lead to the corresponding amine.

Figure 2:
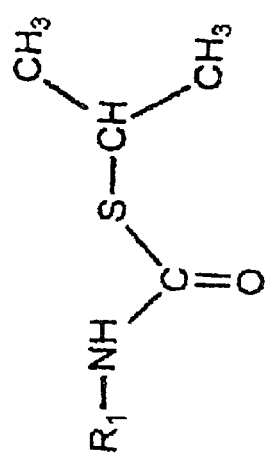
FIG. 2 shows the equation of the reaction of an isocyanate to a thiol function
Figure 2:
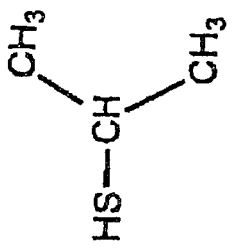
Figure 2:

As can be seen in FIG. 2, the mechanism for the reaction of an isocyanate with a thiol that is difficult to detect (here 2-isopropane thiol) leads, in a basic aqueous environment at an ambient temperature, to the formation of a thiocarbamate thus rendered detectable.

Taking into account the well known reactivity of the isocyanates to water, it was not very plausible to imagine that the traces of thiols, phenols, oximes, or amines (in a concentration between $10^{-11}$ and $10^{-2}$ M) in an aqueous solution, are likely to react quantitatively with an uncombined or intermediate isocyanate (thus coming from the decomposition of a nitrosourea), in order to form a detectable molecule, thiocarbamate, carbamate, or urea.

According to the process of the invention, it thus becomes possible, in an aqueous solution, to quantitatively derive the thiols, phenols, oximes, or amines, alone or in a mixture, in causing the nucleophilic functions to react with an uncombined isocyanate R1—N=C=O or a masked isocyanate (nitrosourea having the general formula: R1NH—CO—NONR2), in order to obtain a derivative having the general formula: R1NH—CO—XR', with XR'=NHR' or OR' or SR' or O—N=R'. It is this derivative that is then quantitatively analyzed by methods known to the expert.

This reaction allows implementing, for example, the process for quantitatively analyzing the nucleophilic functions using either uncombined isocyanates, or nitrosourea as a reservoir of isocyanates, thus used in a stable masked form.

A series of examples of reactions based on this process is given in the following pages. In the examples, we will use several terms having the following formulas

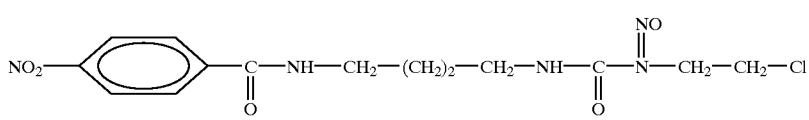

CENU1

Figure 3A:
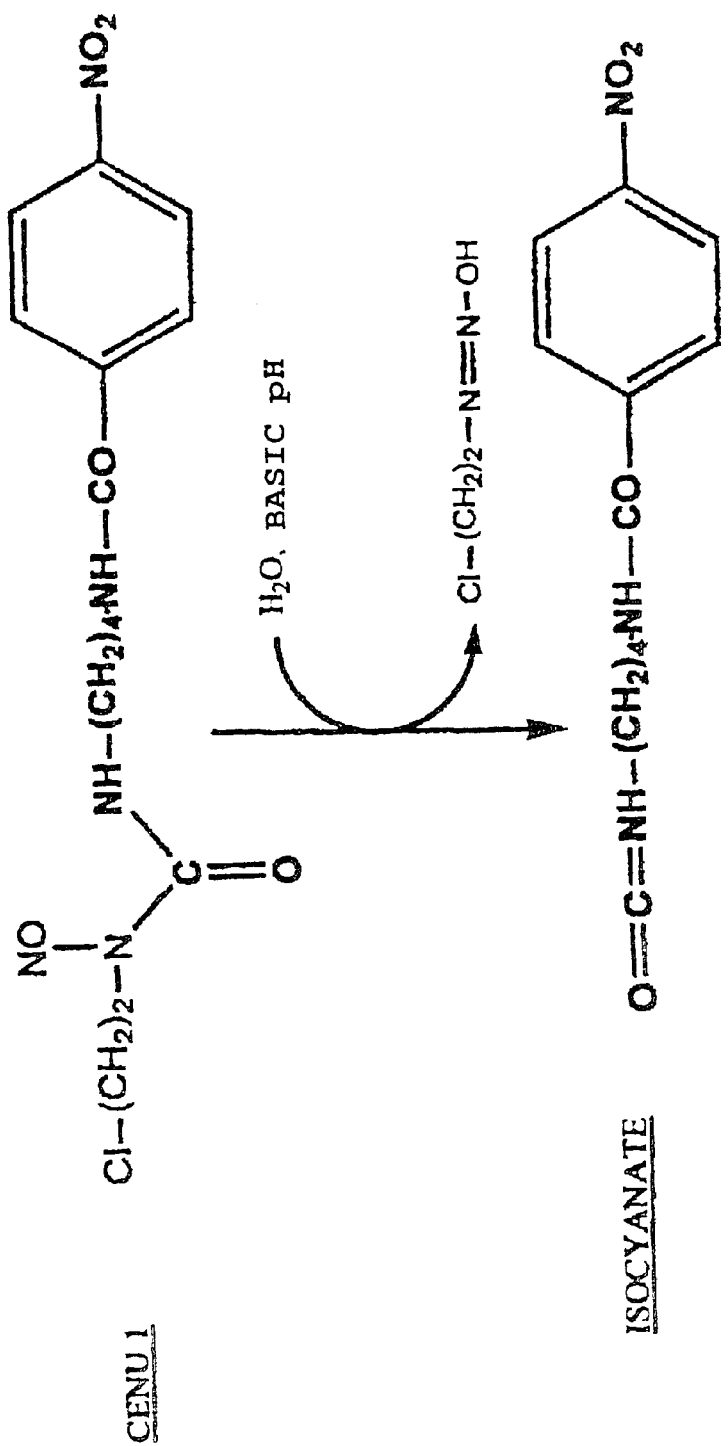
FIG. 3 shows the reaction diagram of the derivation of histamine by chloroethyinitrosourea (CENU1).
Figure 3B:
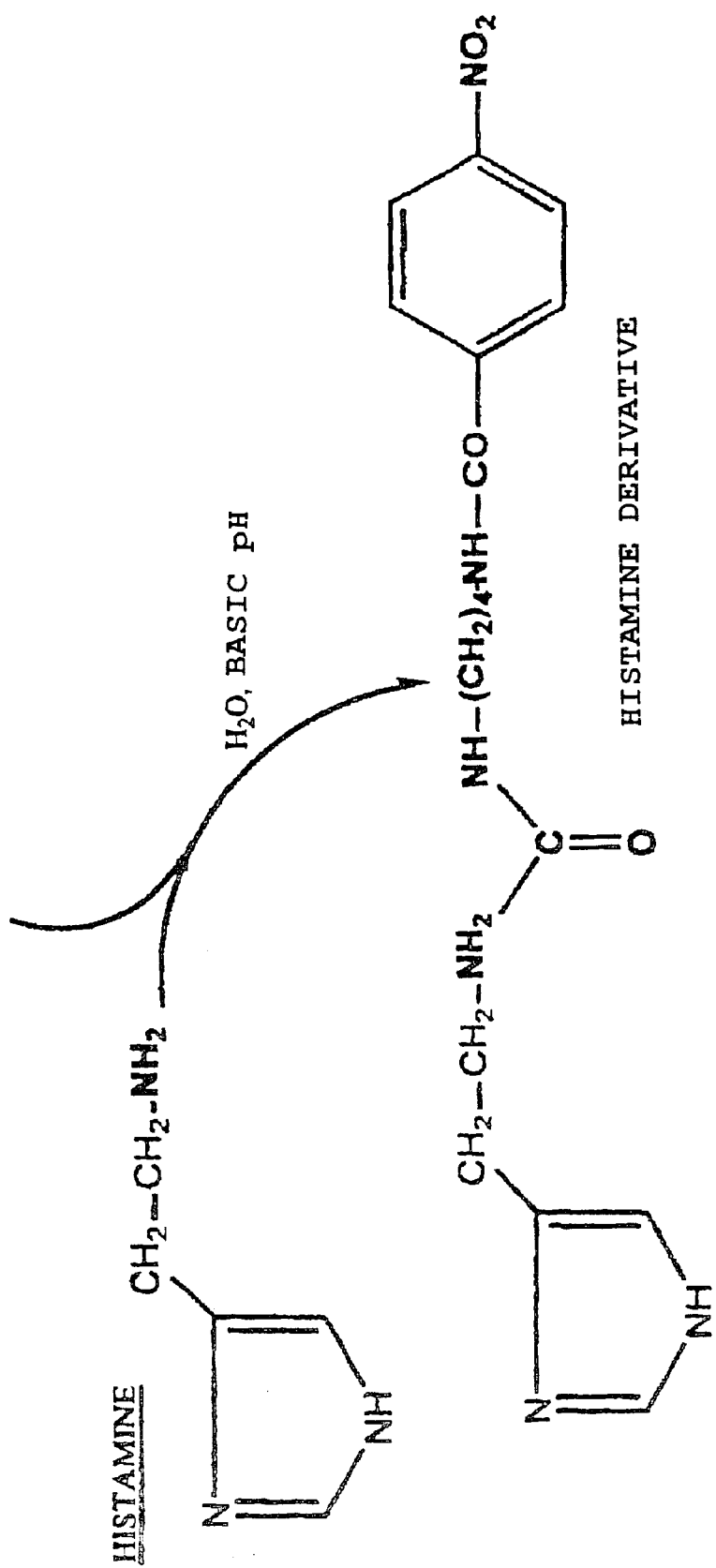

N-p Nitrobenzoyl N'[N-(2-Chloroethyl)-N-nitroso] carbamoyl-1,4-diaminobutane A reaction based on what has just been described is shown in FIG. 3, as far as the case of CENU1 used to derive the histamine is concerned.

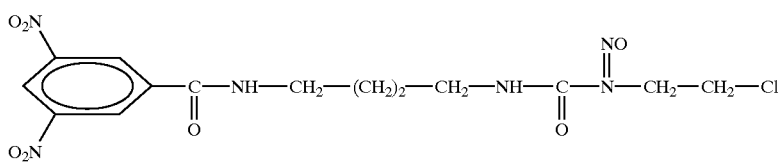

CENU2

N-2,4 Dinitrobenzoyl N'[N-(2-chloroethyl)-N-nitroso] Carbamoyl-1,4-diaminobutane Butyl isocyanate:

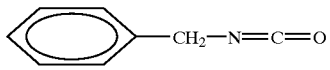

3-isopropenyl- α,α dimethylbenzyl Isocyanate

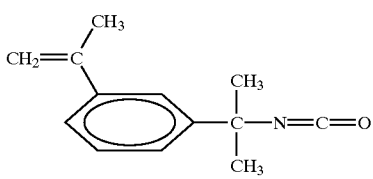

2,4- Dimethoxyphenyl isocyanate

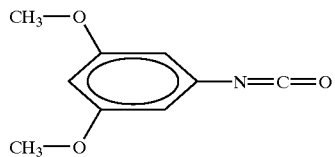

EXAMPLE 1

Put a 10 ml sample of an aqueous solution of histamine (0.2 mM) in a tube. Bring the pH to 10±0.1 with soda 0.1 N. Add 10 ml of a solution of CENU1 in acetonitrile (1.2 mM). The mixture is agitated by ultrasound for 15 minutes at a temperature of 60° C. The derivation is done at the end of this time. The molecule to be quantitatively analyzed has the structure given in the reactional diagram. The quantitative analysis is done by injecting 10 μl of the solution obtained previously by high performance liquid chromatography (column inverted phase C18, acetonitrile/water elution solvent, 68% isocratic, acetonitrile for 10 minutes), U.V. detection at 271 nm. The derivation yield corresponds to the relation between the concentrations quantitatively measured after derivation and those that were expected theoretically. The yield is 75.1%±0.69%.

EXAMPLE 2

Put a 10 ml sample of an aqueous solution of histamine (0.2 mM) in a tube. Bring the pH to 9±0.1 with soda 0.1 N. Add 10 ml of a solution of CENU1 in acetonitrile (1.2 mM). The mixture is agitated by ultrasound for 60 minutes at a temperature of 60° C. The quantitative analysis is done by high performance liquid chromatography.

The derivation yield is 75%±2.9%.

EXAMPLE 3

Put a 10 ml sample of an aqueous solution of histamine (0.2 mM) in a tube. Bring the pH to 9±0.1 with soda 0.1 N. Add 10 ml of a solution of CENU1 in acetonitrile (1.2 mM). The mixture is agitated by ultrasound for 15 minutes at a temperature of 75° C. The quantitative analysis is done by high performance liquid chromatography.

The derivation yield is 75%±3.7%.

EXAMPLE 4

Put a 10 ml sample of an aqueous solution of histamine (0.3 mM) in a tube. Bring the pH to 10±0.1 with soda 0.1 N. Add 10 ml of a solution of CENU1 in acetonitrile (1.2 mM). The mixture is agitated by ultrasound for 15 minutes at a temperature of 75° C. The quantitative analysis is done by high performance liquid chromatography.

The derivation yield is 93.7%±0.35%.

EXAMPLE 5

Put a 10 ml sample of an aqueous solution of histamine (0.3 mM) in a tube. Bring the pH to 9±0.1 with soda 0.1 N. Add 10 ml of a solution of CENU1 in acetonitrile (1.2 mM). The mixture is agitated by ultrasound for 60 minutes at a temperature of 75° C. The quantitative analysis is done by high performance liquid chromatography.

The derivation yield is 86.7%±0.62%.

EXAMPLE 6

Put a 20 ml sample of an aqueous solution of histamine (18 μM) in a tube. Bring the pH to 10±0.1 with soda 0.1 N. Add 20 ml of a solution of CENU 1in acetonitrile (2.16 mM). The mixture is agitated by ultrasound for 15 minutes at a temperature of 60° C. The quantitative analysis is done by high performance liquid chromatography.

The derivation yield is greater than 99%±6%. The quantitative analysis is done again after 22 days in order to check the stability of the histamine derivative. The yield after 22 days (storage at ambient temperature and in light) is greater than 99%±6%.

EXAMPLE 7

Put a 20 ml sample of an aqueous solution of histamine (135 μM) in a tube. Bring the pH to 10±0.1 with soda 0.1 N. Add 20 ml of a solution of CENU1 in acetonitrile (2.16 mM). The mixture is agitated by ultrasound for 15 minutes at a temperature of 60° C. The quantitative analysis is done by high performance liquid chromatography.

The derivation yield is greater than 99%±6%. The quantitative analysis is done again after 22 days in order to check the stability of the histamine derivative. The yield after 22 days (storage at ambient temperature and in light) is greater than 99%±6%.

EXAMPLE 8

Put a 20 ml sample of an aqueous solution of histamine (270 μM) in a tube. Bring the pH to 10±0.1 with soda 0.1 N. Add 20 ml of a solution of CENU1 in acetonitrile (2.16 mM). The mixture is agitated by ultrasound for 15 minutes at a temperature of 60° C. The quantitative analysis is done by high performance liquid chromatography.

The derivation yield is greater than 99%±6%. The quantitative analysis is done again after 22 days in order to check the stability of the histamine derivative. The yield after 22 days (storage at ambient temperature and in light) is greater than 99%±6%.

EXAMPLE 9

Put a 20 ml sample of an aqueous solution of histamine (9.2 μM) in a tube. Bring the pH to 10±0.1 with soda 0.1 N. Add 20 ml of a solution of CENU2 in acetonitrile (2.16 mM). The mixture is agitated by ultrasound for 15 minutes at a temperature of 60° C. The quantitative analysis is done by high performance liquid chromatography.

The derivation yield is greater than 99%±18%. The quantitative analysis is done again after 20 days in order to check the stability of the histamine derivative. The yield after 7 days (storage at ambient temperature and in light) is 98%±19%.

EXAMPLE 10

Put a 20 ml sample of an aqueous solution of histamine (270 μM) in a tube. Bring the pH to 10±0.1 with soda 0.1 N. Add 20 ml of a solution of CENU2 in acetonitrile (2.16 mM). The of mixture is agitated by ultrasound for 15 minutes at a temperature of 60° C. The quantitative analysis is done by high performance liquid chromatography.

The derivation yield is greater than 99%±18%. The quantitative analysis is done again after 8 days in order to check the stability of the histamine derivative. The yield after 7 days (storage at ambient temperature and in light) is 9%±19%.

EXAMPLE 11

Put a 10 ml sample of an aqueous solution of histamine (22 μM) in a tube. Bring the pH to 10.2±0.1 with soda 0.1 N. Add 10 ml of a solution of CENU1 in acetonitrile (2.75 mM). The mixture is agitated by ultrasound for 15 minutes at a temperature of 60° C. The quantitative analysis is done by high performance liquid chromatography.

The derivation yield is greater than 99%±4.4%. The quantitative analysis is done again after 14 days in order to check the stability of the derivative. The yield after 14 days (storage at ambient temperature and in light) is 93%±4.8% (statistically identical to the yield measured immediately after derivation over 6 repetitions).

EXAMPLE 12

Put a 10 ml sample of an aqueous solution of histamine (113 μM) in a tube. Bring the pH to 10.1±0.1 with soda 0.1 N. Add 10 ml of a solution of CENU1 in acetonitrile (2.75 mM). The mixture is agitated by ultrasound for 15 minutes at a temperature of 60° C. The quantitative analysis is done by high performance liquid chromatography.

The derivation yield is greater than 99%±4.4%. The quantitative analysis is done again after 14 days in order to check the stability of the derivative. The yield after 14 days (storage at ambient temperature and in light) is greater than 99%±4.8%.

EXAMPLE 13

Put a 10 ml sample of an aqueous solution of histamine (340 μM) in a tube. Bring the pH to 10±0.1 with soda 0.1 N. Add 10 ml of a solution of CENU1 in acetonitrile (2.75 mM). The mixture is agitated by ultrasound for 15 minutes at a temperature of 60° C. The quantitative analysis is done by high performance liquid chromatography.

The derivation yield is greater than 99%±4.4%. The quantitative analysis is done again after 14 days in order to check the stability of the derivative. The yield after 14 days (storage at ambient temperature and in light) is greater than 99%±4.8%.

EXAMPLE 14

Put a 10 ml sample of an aqueous solution of cadaverine (20 μM) in a tube. Bring the pH to 10±0.1 with soda 0.1 N. Add 10 ml of a solution of CENU1 in acetonitrile (2.75 mM). The mixture is agitated by ultrasound for 15 minutes at a temperature of 60° C. The quantitative analysis is done by high performance liquid chromatography.

The derivation yield is 50%±2.6%. The quantitative analysis is done again after 8 days in order to check the stability of the derivative. The yield after 14 days (storage at ambient temperature and in light) is 50%±2%.

EXAMPLE 15

Put a 10 ml sample of an aqueous solution of cadaverine (313 μM) in a tube. Bring the pH to 10±0.1 with soda 0.1 N. Add 10 ml of a solution of CENU1 in acetonitrile (2.75 mM). The mixture is agitated by ultrasound for 15 minutes at a temperature of 60° C. The quantitative analysis is done by high performance liquid chromatography.

The derivation yield is 55%±2.6%. The quantitative analysis is done again after 8 days in order to check the stability of the derivative. The yield after 14 days (storage at ambient temperature and in light) is 54%±2%.

EXAMPLE 16

Add 10 μl of benzoyl isocyanate to 50 ml of an aqueous solution of isopropoxyphenol (1.6 mM) previously basified to a pH of 10±0.1 with soda 0.1 N. The mixture is agitated for 2 hours at ambient temperature by traditional mechanical agitation. After quantitative analysis by high performance liquid chromatography using U.V. detection, the derivation yield calculated is 67%±3%.

EXAMPLE 17

Add 10 µl of benzoyl isocyanate to 50 ml of an aqueous solution of isopropoxyphenol (1.6 mM) previously basified to a pH of 9±0.1 with soda 0.1 N. The mixture is agitated for 2 hours at ambient temperature by traditional mechanical agitation. After quantitative analysis by high performance liquid chromatography using U.V. detection, the derivation yield calculated is 36%±2.9%.

EXAMPLE 18

Add 10 µl of benzoyl isocyanate to 50 ml of an aqueous solution of naphthol (1.6 mM) previously basified to a pH of 8±0.1 with soda 0.1 N. The mixture is agitated for 2 hours at ambient temperature by traditional mechanical agitation. After quantitative analysis by high performance liquid chromatography using U.V. detection, the derivation yield calculated is 64%±3.4%.

EXAMPLE 19

Add 10 µl of benzoyl isocyanate to 50 ml of an aqueous solution of naphthol (1.6 mM) previously basified to a pH of 8±0.1 with soda 0.1 N. The mixture is agitated for 6 hours at ambient temperature by traditional mechanical agitation. After quantitative analysis by high performance liquid chromatography using U.V. detection, the derivation yield calculated is 75%±3.4%.

EXAMPLE 20

Add 10 µl of benzoyl isocyanate to 50 ml of an aqueous solution of naphthol (1.6 mM) previously basified to a pH of 9±0.1 with soda 0.1 N. The mixture is agitated for 2 hours at ambient temperature by traditional mechanical agitation. After quantitative analysis by high performance liquid chromatography using U.V. detection, the derivation yield calculated is 69%±3.4%.

EXAMPLE 21

Add 10 µl of benzoyl isocyanate to 50 ml of an aqueous solution of oxime (1.62 mM) previously basified to a pH of 8±0.1 with soda 0.1 N. The mixture is agitated for 5 hours at ambient temperature by traditional mechanical agitation. After quantitative analysis by high performance liquid chromatography using U.V. detection, the derivation yield calculated is 45%±2.3%.

EXAMPLE 22

Add 10 µl of benzoyl isocyanate to 50 ml of an aqueous solution of oxime (1.62 mM) previously basified to a pH of 8±0.1 with soda 0.1 N. The mixture is agitated for 20 hours at ambient temperature by traditional mechanical agitation. After quantitative analysis by high performance liquid chromatography using U.V. detection, the derivation yield calculated is 46%±2.3%.

EXAMPLE 23

Add 25 µl of benzoyl isocyanate to a mixture of isopropanethiol (1.8 mM), isopropylamine (1.75 mM), acetone oxime (1.7 mM) in a solution of 50% acetonitrile and 50% double buffered boric acid and potassium tartrate adjusted to a pH of 10 with soda N/5. Everything is agitated for 2 hours at ambient temperature (mechanical agitation).

The derivation yields obtained after quantitative analysis by high performance liquid chromatography are: greater than 99%±5%, 33%±8%, 86%±10%, respectively for isopropylamine, oxime, and isopropanethiol.

EXAMPLE 24

Add 25 µl of benzoyl isocyanate to a mixture of isopropanethiol (0.93 mM), isopropylamine (0.87 mM), acetone oxime (0.85 mM) in a solution of 50% acetonitrile and 50% double buffered boric acid and potassium tartrate adjusted to a pH of 10 with soda N/5. Everything is agitated for 2 hours at ambient temperature (mechanical agitation).

The derivation yields obtained after quantitative analysis by high performance liquid chromatography are: greater than 99%±5%, 42%±8%, 85%±6%, respectively for isopropylamine, oxime, and isopropanethiol.

EXAMPLE 25

Add 25 µl of benzoyl isocyanate to a mixture of isopropanethiol (1.8 mM), isopropylamine (1.75 mM), acetone oxime (1.7 mM) in a solution of 50% acetonitrile and 50% double buffered boric acid and potassium tartrate adjusted to a pH of 9 with soda N/5. Everything is agitated for 2 hours at ambient temperature (mechanical agitation).

The derivation yields obtained after quantitative analysis by high performance liquid chromatography are: greater than 99%±5%, 73%±8%, 99%±6%, respectively for isopropylamine, oxime, and isopropanethiol.

EXAMPLE 26

Add 25 µl of benzoyl isocyanate to a mixture of isopropanethiol (0.93 mM), isopropylamine (0.87 mM), acetone oxime (0.85 mM) in a solution of 50% acetonitrile and 50% double buffered boric acid and potassium tartrate adjusted to a pH of 9 with soda N/5. Everything is agitated for 2 hours at ambient temperature (mechanical agitation).

The derivation yields obtained after quantitative analysis by high performance liquid chromatography are: greater than 99%±5%, 79%±8%, 93%±6%, respectively for isopropylamine, oxime, and isopropanethiol.

EXAMPLE 27

Take a sample of 10 ml of a solution of 10% water and 90% acetonitrile containing 0.13 mM methylamine, 0.14 mM acetone oxime, 0.067 mM diisopropylamine, 0.1 mM isopropanethiol and 0.067 naphthol. Add 24 µl of 3-isopropenyl-α,α-dimethylbenzyl isocyanate and 18 µl of triethylamine (pH~10.7) and agitate the solution mechanically for 2 hours at ambient temperature.

The derivation yields obtained after quantitative analysis by high performance liquid chromatography are: 72%±2%, 7%±5%, 9%±2%, greater than 99%±6% and 5%±1%, respectively for methylamine, acetone oxime, isopropanethiol, diisopropylamine and naphthol.

EXAMPLE 28

Take a sample of 10 ml of a solution of 30% water and 70% acetonitrile containing 0.14 mM acetone oxime, 0.057 mM diisopropylamine, 0.1 mM isopropanethiol and 0.067 naphthol. Add 24 µl of 3-isopropenyl-α,α-dimethylbenzyl isocyanate and 18 µl of triethylamine (pH~10.4) and agitate the solution mechanically for 2 hours at ambient temperature.

The derivation yields obtained after quantitative analysis by high performance liquid chromatography are: 11%±2%, 32%±1.5%, 93%±2%, 24%±0.3%, respectively for acetone oxime, isopropanethiol, diisopropylamine and naphthol.

EXAMPLE 29

Take a sample of 10 ml of a solution of 50% water and 50% acetonitrile containing 0.14 mM acetone oxime, 0.057 mM diisopropylamine, 0.1 mM isopropanethiol and 0.067 mM naphthol. Add 24 µl of 3-isopropenyl-α,α-dimethylbenzyl isocyanate and 18 µl of triethylamine (pH~10.6) and agitate the solution mechanically for 2 hours at ambient temperature.

The derivation yields obtained after quantitative analysis by high performance liquid chromatography are: 20%±1%, 79%±1.1%, greater than 99%±2.8%, 83%±2%, respectively for acetone oxime, isopropanethiol, diisopropylamine and naphthol.

EXAMPLE 30

Take a sample of 10 ml of a solution of 50% water and 50% acetonitrile containing 0.13 mM methylamine, 0.14 mM acetone oxime, 0.057 mM diisopropylamine, 0.1 mM isopropanethiol, 0.067 naphthol, and 0.076 mM isopropoxyphenol. Add 0.06 mmole of 2,4- dimetoxyphenyl isocyanate and 4 µl of triethylamine (pH~8.6) and agitate the solution mechanically for 1 hour at ambient temperature.

The derivation yields obtained after quantitative analysis by high performance liquid chromatography are: 41%±3%, 31%±2.8%, 44%±3%, 64%±5%, 72%±3.5%, 30%±1.8%, respectively for methyl amine, acetone oxime, diisopropylamine, isopropanethiol, naphthol and isopropoxyphenol.

EXAMPLE 31

Take a sample of 20 ml of a solution of 50% water and 50% acetonitrile containing 0.13 mM methylamine, 0.14 mM acetone oxime, 0.008 mM diisopropylamine, and 0.007 naphthol.

Add 30 µl of 3-isopropenyl-α,α-dimethylbenzyl isocyanate and 20 µl of triethylamine (pH~11.1) and agitate the solution mechanically for 2 hours at ambient temperature.

The derivation yields obtained after quantitative analysis by high performance liquid chromatography are: 87%±2.7%, 22%±2.6%, 82%±3%, 99%±8%, respectively for methylamine, acetone oxime, naphthol and diisopropylamine.

Carry out an extraction of the compounds contained in the remnant of the mixture by salt (1 g of NaCl for 10 ml of solution of 50% water and 50% acetonitrile). The salt causes the transition of compounds in the acetonitrile which separate from water. Measure the volume of the acetonitrile separated in this manner and measure again the derived compounds by chromatography after 29 hours of storage at ambient temperature. The yields calculated are: 87%, 44%, 83%, greater than 99%, respectively for methylamine, acetone oxime, naphthol and diisopropylamine. Extraction is thus total and the compounds are stable.

EXAMPLE 32

Take a sample of 20 ml of a solution of 50% water and 50% acetonitrile containing 0.13 mM methylamine, 0.14 mM acetone oxime, 0.103 mM isopropanethiol, 0.08 mM diisopropylamine, and 0.07 mM naphthol. Add 30 µl of 3-isopropenyl-α,α-dimethylbenzyl isocyanate and 20 µl of triethylamine (pH~11.1) and agitate the solution mechanically for 2 hours at ambient temperature. The derivation yields obtained after quantitative analysis by high performance liquid chromatography are: 86%±2.3%, 21%±2.6%, greater than 99%±5%, 75% 25±3.2%, and greater than 99%±7%, respectively for methylamine, acetone oxime, isopropanethiol, naphthol and diisopropylamine.

After extraction with NaCl (1 g of NaCl per 10 ml of mixture), and 29 hours of storage at ambient temperature, the yields obtained are statistically identical to those initially measured which show that the derivatives are stable in these conditions.

EXAMPLE 33

Take a sample of 20 ml of a solution of 50% water and 50% acetonitrile containing 0.066 mM methylamine, 0.072 mM acetone oxime, 0.052 mM isopropanethiol, 0.04 mM diisopropylamine, and 0.035 mM naphthol. Add 30 µl of 3-isopropenyl-α,α-dimethylbenzyl isocyanate and 20 µl of triethylamine (pH~11.1) and agitate the solution mechanically for 2 hours at ambient temperature. The derivation yields obtained after quantitative analysis by high performance liquid chromatography are: 84%±2.5%, 20%±2%, greater than 99%±6%, 76%±3.1%, and 98%±6%, respectively for methylamine, acetone oxime, isopropanethiol, naphthol and diisopropylamine.

After extraction with NaCl (1 g per 10 ml of mixture), and 29 hours of storage at ambient temperature, the yields obtained are statistically identical to those initially measured which show that the derivatives are stable in these conditions.

EXAMPLE 34

Take a sample of 20 ml of a solution of 50% water and 50% acetonitrile containing variable concentrations of methylamine, diisopropylamine, acetone oxime, isopropanethiol, and naphthol consisting of between $10^{-3}$ M and $10^{-7}$ M. Add 30 µl of 3-isopropenyl-α,α-dimethylbenzyl isocyanate and 20 µl of triethylamine. Agitate the solution mechanically for at least one hour at ambient temperature. The derivatives formed are quantitatively analyzed by high performance liquid chromatography. The yields are constant whatever the initial concentration of nucleophiles and are: 100%±4.15 100±6.98, 20±2.2, 82±4.68, and 60±6.2.

FUNCTIONAL MODE

The functional mode of the process follows directly from its description.

The components of a quantitative analysis kit for histamine are:

1. A flask of N-2,4 dinitrobenzoyl N'[N-(2-chloroethyl)-N-nitroso]carbamoyl-1,4-diaminobutane in the form of a pure powder 99%.
2. A triethylamine solution at 99%.
3. A grafting column C18.
4. A standard of pure histamine derivative with its RMN and UV spectrum
5. Solutions in acetonitrile of the standard histamine derivative to be used for calibration of the system.
6. Chromatographical method with an example of a chromatogram.
7. Usage protocol of the kit: containing detailed description of the operations to be performed and the precision of the measurements (according to statistical tests with the supplied material).

The use of this quantitative analysis kit, completed by the usual laboratory equipment (syringes, pipettes, etc. . . ) is carried out according to the examples given above.

ADVANTAGES OF THE INVEVENTION

The major advantage is the effective derivation in a single reaction of a large number of carrier compounds of nucleophilic functions, thus becoming easily detectable. The compounds that can be derived by this method are for example:

carbamates thiocarbamates dithiocarbamates carbanilates amides amino acids proteins aromatic amines biogenic amines aliphatic amines ureas and substituted ureas chlorophenols phenols pichloram and other derivatives of pyridine containing an amine or a phenol triazines herbicides from the uracil family chloroacetamides amitrols certain dinitroanilines (Butraline, Penoxaline . . . )

The compounds that can be quantitatively analyzed by this method are generally all of the products containing one of the functions oxime, phenol, thiol or primary or secondary amines. These functions can be uncombined or masked. In the case of masked functions (involved in a covalent or non-covalent chemical bond), it is necessary to unmask them. Thus, in the case of carbamates that are a family of pesticides, it is possible by simple basic hydrolysis by heat (a known process) to uncombine the aforementioned nucleophilic functions.

According to the process of the present invention, it is possible to create low cost devices having numerous applications for quantitatively analyzing pollutants present only in trace amounts in an aqueous environment. There are numerous "micro-pollutants" in the environment that have thiol, phenol, oxime or amine groups. It is possible to manufacture kits for quantitative analysis of the freshness of food products by the method of the present invention. Similarly, the identification of trace amounts of pesticides in an aqueous environments can also be carried out.

Finally, as has been seen above, the known derivative agents are fragile in storage, while the use of nitrosourea makes it possible to create devices that can be stored for a long time without deterioration of their performances. Typically, there was practically no deterioration of stored powder nitrosourea over time, and storage in a solution did not cause any real deterioration over a duration on the order of one month.

The scope of the invention presented here is not limited to the embodiment modes but extends, on the contrary to perfections and modifications within the range of the professional. Applications for the purification or the extraction of molecules are for example, directly derivable from the examples described.

We claim:

1. A process for analyzing a mixture having at least one compound represented by a formula HR3 which bears a nucleophilic group in a trace amount in an aqueous medium, R3 being a monovalent radical selected from the group consisting of —NHR', —NR'R", —OR', —SR' or —O—N=R" where R' and R" are monovalent radicals, the process comprising:

adding at least a precursor compound of an isocyanate to a basic aqueous solution containing at least the compound represented by the formula HR3 in a trace amount, said precursor compound being R1NH—CO—N(NO)—R2 where R1 is an aliphatic or aromatic radical;

decomposing the precursor compound added solution in an aqueous basic medium into an isocyanate compound of formula R1—N=CO;

reacting the decomposed solution at a temperature of less than 100° C. inclusive for a period of time of between 10 and 120 minutes inclusive; and quantitatively analyzing reaction products of the compound of the formula HR3 and the isocyanate compound of formula R1—N=CO.

2. The process of claim 1, wherein the compound R1NH—CO—N(NO)—R2 is selected from the group consisting of CENU1 and the CENU2 wherein R1 is the radical —$(CH_2)_4$ NH—CO—$C_6H_5$—$NO_2$ and R2 is the radical —$(CH_2)_2$—Cl and respectively R1 is the radical —$(CH_2)_4$ NH—CO—$C_6H_5$—$(NO_2)_2$ and R2 is the radical —$(CH_2)_2$—Cl.

3. The process of claim 1, wherein the reacted solution is maintained at a temperature between 5° C. and 100° C.

4. The process of claim 1, wherein said basic aqueous solution has a pH of between 8 and 11 inclusive.

5. The process of claim 1, wherein the mixture selected from the group consisting of phenols, thiols, primary and secondary amines, oximes, the mixtures thereof, histamine, putrescine, cadaverine, benzyl isocyanate, a mixture of isopropanethiol, isopropylamine and acetoxime, a mixture of methylamine, acetoxime, diisopropylamine, isopropanethiol and naphthol, a mixture of acetoxime, diisopropylamine, isopropanethiol and naphthol, a mixture of methylamine, acetoxime, diisopropylamine, isopropanethiol, naphthol and isopropoxyphenol.

* * * * *